(12) United States Patent
Majeed et al.

(10) Patent No.: US 6,794,537 B1
(45) Date of Patent: Sep. 21, 2004

(54) MANUFACTURING PROCESSES FOR SE-METHYL-L-SELENOCYSTEINE

(75) Inventors: Muhammed Majeed, Piscataway, NJ (US); Kalyanam Nagabhushanam, North Brunswick, NJ (US); Rajendran Ramanujam, Bangalore (IN); Ravikrishna Chebolu, North Brunswick, NJ (US); Keshava Rapole, Edison, NJ (US)

(73) Assignee: Sami Labs Limited, Bangalore (IN)

( * ) Notice: Subject to any disclaimer, the term of this patent is extended or adjusted under 35 U.S.C. 154(b) by 0 days.

(21) Appl. No.: 10/065,677

(22) Filed: Nov. 7, 2002

(51) Int. Cl.[7] .................. C07B 55/00; C07C 391/00
(52) U.S. Cl. ....................... 562/401; 562/899
(58) Field of Search ..................... 562/401, 899, 562/556

(56) References Cited

U.S. PATENT DOCUMENTS 3,678,067 A * 7/1972 Grummon et al.
4,401,820 A * 8/1983 Chibata et al.

OTHER PUBLICATIONS

Andreadou et al, Journal of Medicinal Chemistry, 1996, 39(10), pp. 2040–2046.*

Walsh et al, The Journal of Biological Chemistry, Studies on the Mechanism of D–Amino Oxidase, 1971, 246(22), pp. 6855–6866.*

Patai, The Chemistry of the Carbon–Halogen Bond, Part 1, 1973, John Wiley & Sons, New York, pp. 463–466.*

* cited by examiner

Primary Examiner—Johann Richter
Assistant Examiner—Paul A. Zucker

(57) ABSTRACT

Convenient processes are described for the synthesis of L-Se-methyselenocysteine from chloroalanine derivatives. The process is easily extendable to other selenium substituted amino acids. DL-Se-methyselenocysteine is easily obtained by a benzaldehyde-catalyzed racemization of L-Se-methyselenocysteine.

8 Claims, 2 Drawing Sheets

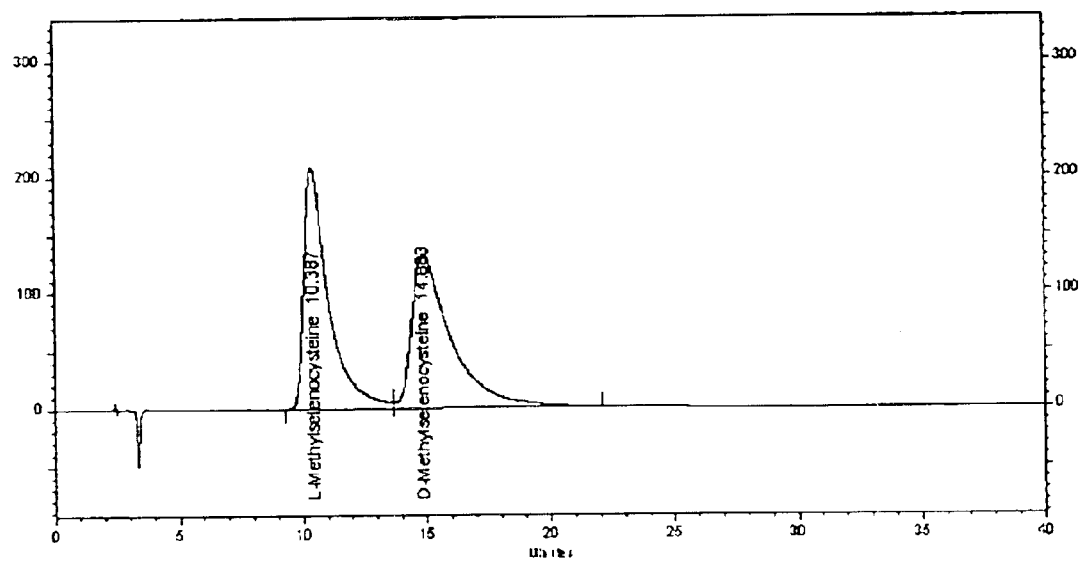
Figure 1. Chiral HPLC of DL-Se-Methylselenocysteine

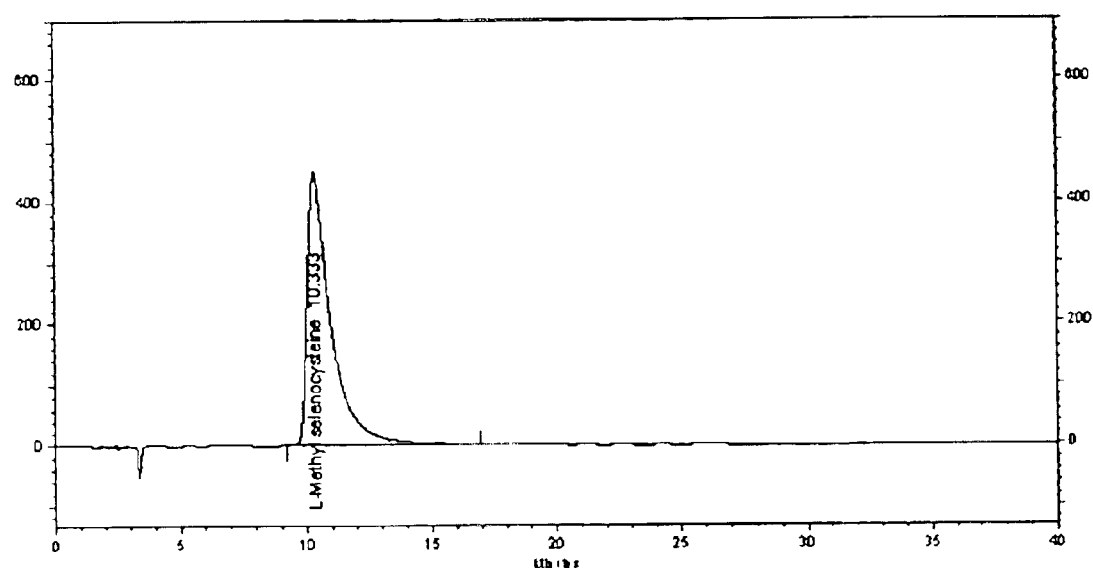
Figure 2. Chiral HPLC of L-Se-Methylselenocysteine

MANUFACTURING PROCESSES FOR SE-METHYL-L-SELENOCYSTEINE

BACKGROUND OF INVENTION

Selenium is an essential micronutrient for the well being of humans. Lack of adequate amounts of selenium results in various diseases and deficiencies (Rayman, M. P.; Lancet, 2000, 356, 233–241) Selenium is present naturally in several plant and animal foods. Brazil nuts, walnuts, grains, meat and sea food are good sources (Facts about dietary supplements—Selenium, NIH, 2001) . Dietary exposure from these sources varies with geographical location, depending upon the selenium content in the soil. Situations where adequate amounts of selenium cannot be obtained from natural resources warrant the use of selenium supplements. Such selenium supplements include organic forms (such as selenium yeast L-Selenomethionine) and Sodium selenite, an inorganic form that is not well utilized (Schrauzer, G. N.; J. Med. Foods, 1998, 1, 201–206.). One important selenium supplement is L-Se-methylselenocysteine (L-Methylselenocysteine, L-Se-methylselenocysteine or L-MSC as abbreviated in this patent).

L-MSC is a selenoamino acid found naturally in vegetables such as garlic and broccoli. It is a bioavailable and safe form of supplementing the essential trace mineral nutrient, selenium. Selenium in the form of Selenocysteine is an essential component of antioxidant enzymes such as glutathione peroxidase and is also found in several proteins in the body. Antioxidant enzymes containing selenium, protect cells against oxidative damage (Cronin, J. R.; Alt. Complement. Therap. 2000, 6(6), 342–346).

Studies in animal models have shown that L-MSC is effective in cancer chemoprevention. A monomethylated selenium metabolite is reported to be essential for cancer chemoprevention (Ip, C. et al.; Cancer Res. 2001, 60(11), 2882–2886). Selenium-enriched garlic is reported to be useful as a nutritional supplement in the prevention of cancer and contains L-MSC which is a major constituent of plants grown on Selenium rich media (Ip, C. and Lisk, D.; J. Nutr. and Cancer, 2001, 28(2), 184–188). It is one of the most effective chemopreventive forms of selenium. Studies indicate that it does not get incorporated into proteins, thereby minimizing the possibility of excessive accumulation in tissues (Ip, C. et al.; Selenium In Biology and Human Health; Burk, R. F. Ed; 1994,169 180).

SCOPE OF THE INVENTION

The present patent describes efficient processes for the manufacture of L-Se-methyselenocysteine, D-Se-methylselenocysteine and DL-Se-methylselenocysteine: The structures of the referred materials are shown below;

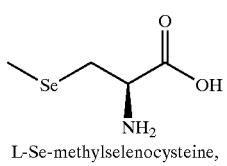
L-Se-methylselenocysteine,

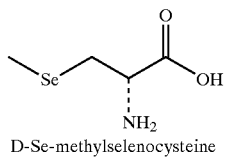
D-Se-methylselenocysteine

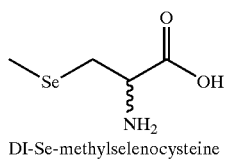
DI-Se-methylselenocysteine

RELATED PRIOR ART

L-Se-methylselenocysteine has been prepared from L-chloroalanine and disodiumdiselenide in a two step process (Tanaka, H; Soda, K; Selenocysteine. Methods Enzymol., 1987, 143, 240–243; Andreadou, I; Menge, W. M. P. B.; Commandeur, J. N. M.; Worthington, E. A.; Vermeulen, N. P. E.; J. Med. Chem., 1996, 39, 2040–2046). Broadly in this process chloroalanine is reacted with disodiumdiselenide to give L-selenocystine in the first step. In a subsequent step, the —Se—Se— bond in L-selenocystine is cleaved in liquid ammonia at −70° C. using small pieces of metallic sodium and subsequently alkylated with methyliodide to give L-Se-methylselenocysteine. This process utilizes very low temperature for its reaction and also metallic sodium in small pieces which is hazardous in large scale practice.

In another process (Spallholz, J. E.; Reid, T. W.; Walkup, R. D.; A method of using synthetic L-Se-methylselenocysteine as a nutraceutical and a method of its synthesis, EP 1 205 471, 2001), the synthesis is done by mixing N-(tert-butoxycarbonyl)-L-serine with a dialkyl diazodicarboxylate and at least one of a trialkylphosphine, triarylphosphine and phosphite to form a first mixture that includes N-(tert-butoxycarbonyl)-L-serine β-lactone. Methylselenol or its salt is mixed with the N-(tert-butoxycarbonyl)-L-serine β-lactone to form a second mixture that includes N-(tert-butoxycarbonyl)-Se-methylselenocysteine. The tert-butoxycarbonyl group is removed from the N-(tert-butoxycarbonyl)-Se-methylselenocysteine to form L-Se-methylselenocysteine. In this process, serine is protected with a Boc group and converted to its lactone form which is further reacted with methylselenol or its salt. The protecting group is removed to give L-Se-methylselenocysteine. The method is lengthy and involves expensive protecting groups and reagents.

Lithiated alkenylselenium compounds have been reported to be generated from Grignard reagents and disetenides followed by lithiatlon of the resultant alkenyl-alkyl selenide (Block, E.; Birringer, M.; Jiang, W.; Nakahodo, T.; Thompson, H. J.; Toscano, P. J.; Uzar, H.; Zhang, X.; Zhu, Z.; J Agri. Food Chem., 2001, 49, 458–470)

Grummon et at (U.S. Pat. No. 3,678,067) describes a process for the synthesis of selenomethionine but involves the use of liquid ammonia and sodium. As pointed out already, such processes would be cumbersome to practice routinely Chibata et al (U.S. Pat. No. 4,401,820) teaches a process for the racemization of optically active amino acids using an aromatic aldehyde and aliphatic acid but does not teach or suggest the use of the process for selenium-containing amino acids.

BRIEF DESCRIPTION OF DRAWINGS

FIG. 1 shows the chiral column HPLC of DL-Se-methylselenocysteine showing separate peaks for L-Se-Methylselenocysteine (~10 mts) and D-Se-Methylselenocysteine (~15 mts).

FIG. 2 shows the chiral column HPLC of the sample of L-Se-Methylselenocysteine showing complete absence of the other D-isomer.

DETAILED DESCRIPTION

The invention sought to be patented relates to the synthesis of L-Se-methylselenocysteine (Ia) by reaction with the salt of methylselenol (CH3SeM where M=Na, K etc) with L-Chloroalanine methyl ester hydrochloride (IIa) or with L-Chloroalanine hydrochloride (IIb) or with L-Chloroalanine (IIc).

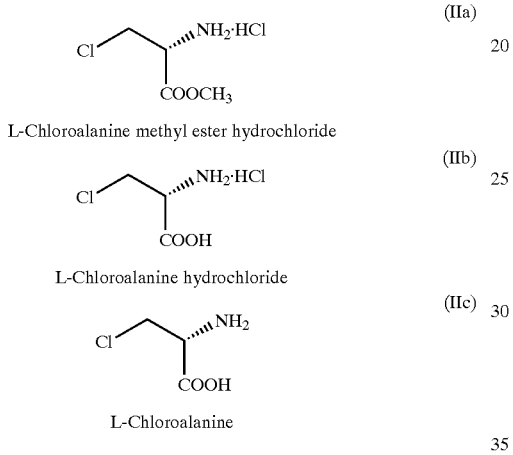

L-Chloroalanine methyl ester hydrochloride (IIa)

L-Chloroalanine hydrochloride (IIb)

L-Chloroalanine (IIc)

L-Chloroalanine methyl ester hydrochloride (IIa) was synthesized by the reaction of L-Serine methyl ester hydrochloride with phosmhorous pentachloride in chloroform solution. The method of Walsh (Walsh, C. T.; Schonbrunn, A.; Abeles, R. H.; J Biol Chem., 1971,246 (22), 6855–6866) is but one way of synthesizing L-Chloroalanine methyl ester hydrochloride (IIa). Alternatively other methods could be used. As mentioned, IIa, IIb and IIc were all convenient raw materials for L-Se-methyl selenocysteine.

Dimethyidiselenide (CH₃SeSeCH₃) was reduced-in basic medium with sodium borohydride to form Methylselenide sodium(CH₃SeNa) in aqueous alkaline solution which can react facilely with IIa or IIb or IIc to give L-Methylselenocysteine which is isolated from the reaction mixture in very good yields. The reaction could be done in water, or dimethyl formamide-water or acetonitrile-water. In the place of sodiumborohydride, one could use other similar variants of sodium borohydride namely potassium borohydride or zinc borohydride or sodium cyanoborohydride or sodium triacetoxy borohydride; depending on the cation methylselenide potassium or methylselenide sodium will be formed.

We also found that hypophosphorous acid could be used to cleave Se—Se— bond of dimethyldiselenide and the sodium salt of methylselenol was formed using sodium hydroxide. The methyselenide sodium thus generated was reacted with L-chloroalanine methyl ester hydrochloride (IIa), or L-chloroalanine hydrochloride (IIb) or L-chloroalanine (IIc) to get L-Se-methylselenocysteine. In extension of the above concept, one can use a dialkyldiselenide as a starting material to generate alkylselenide anion which can react with IIa, IIb or IIc to yield L-Se-alkylselenocysteine. In an analogous way, D-Se-methylselenocysteine (Ib) is obtained from D-Chloroalanine methyl ester hydrochloride (IIIa) or from D-Chloroalanine hydrochloride (IIIb) or from D-Chloroalanine (IIIc). These raw materials IIIa, IIIb and IIIc are obtainable from D-Serine methyl ester hydrochloride in a similar way described for the L-analogs.

By similar process, one can produce other D-Se-alkylselenocysteine. Similarly in an analogous way DL-Se-methylsenocysteine (Ic) is obtained from DL-Chloroanine methyl ester hydrochloride (IVa) or from DL-Chloroalanine hydrochloride (IVb) or from DL-Chloroalanine (IVc). These raw materials are obtained from DL-Serine methyl ester hydrochloride as described for the L-analogs.

Extensions of the described processes to manufacture DL-Se-alkylselenocysteine are possible.

Additionally DL-Se-methylselenocysteine (Ic) is also obtainable from L-Se-methylselenocysteine (Ia) or from D-Se-methylselenocysteine (Ib) by raceimization as the Example 4 described later in this embodiment will illustrate.

L-Se-methylselenocystelne (Ia) obtained by these methods was chirally pure and homogeneous as shown by HPLC methods.

In the examples illustrated it is anticipated that the stereoisomers of bromoalanine (V) or 3-Tosyloxy alanine (VI) or their hydrochloridelhydrobromide salts or esters could also be used and such variations are also covered under this Invention.

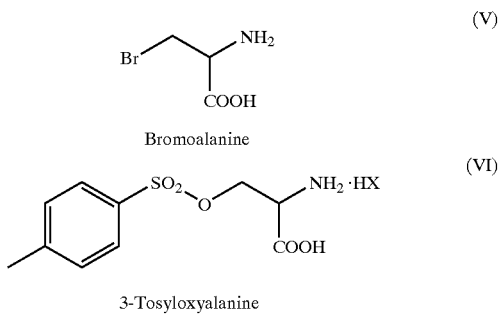

Bromoalanine (V)

3-Tosyloxyalanine (VI)

The following examples will illustrate the utility and practice of this invention. They are provided as illustrating examples only and they do not any way limit the inventions or claims made in this patent.

EXAMPLE 1

L-Se-Methyl Selenocysteine from L-Chloroalanine Hydrochloride

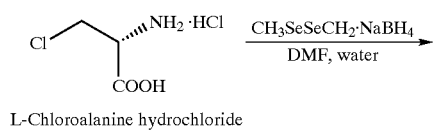

L-Chloroalanine hydrochloride

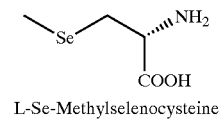

L-Se-Methylselenocysteine

Dimethyldiselenide (50 g) in DMF (20 ml) was taken to get a clear solution. NaOH solution (24 g in 100 ml water) was added under stirring. The mass was cooled to 5–10° C. and to this was added, portion-wise, solid sodium borohydride (6 g) at <10° C. The reaction mixture was warmed to 40–45° C. and maintained for 2 hrs to get a clear colorless solution.

The reaction mass was cooled 5–10° C. and L-Chloroalanine HCl (20 g dissolved in 100 ml water) was added below 10° C. After completion of addition, stirring was continued at RT for 30 mts. The reaction mixture was warmed to 40–45° C. and maintained for 2 hrs. TLC was checked for the completion of the reaction. (Eluent: n-Butanol (6): Acetic acid (2): Water (2); $R_f$ of the starting material is 0.35 and $R_f$ of the product is 0.4). On completion of the reaction, the reaction mixture was cooled to RT and the pH of the reaction mixture adjusted to acidic pH using 6N HCl.

The mass was concentrated under vacuum. Again 6N HCl (100 ml) was added to the mass and stirred well for 15 minutes. Again the mass was concentrated under vacuum to dryness. Methanol was added to the residue and stirred well for 30 mts. The product, L-Se-methylselenocysteine hydrochloride, dissolved in methanol leaving out the salts. The salts were removed by filtration. The pH of the filtrate was adjusted to 6–7 using triethylamine. TEA. The product L-Se-methylselenocysteine was filtered and washed with methanol (50 ml) and sucked dry. The product was further dried under vacuum.

Further purification could be achieved by crystallization from water-ethanol. Yield: 16 g: Melting point: 180–184° C.; Purity by HPLC: >99%; NMR: Proton (solvent D2O, δ values) 2.03 (3H, s); 3.09 (1H, q, J=14.39, 7.2Hz); 3.16 (1H, q, J=14.39, 4.8 Hz); 4.33 (1H, distorted triplet wih fine structure); 4.79 (other exchanging protons) Carbon (solvent D2O, δ values) 4.94 ($CH_3$), 23.77 ($CH_2$), 52.71 (CH), 171.12 (C=O). Elemental analysis: Calculated for $C_4H_9NO_2Se$ and calculated (% values in parenthesis): C:26.35 (26.39); H:4.93 (4.98); N:7.64 (7.69); Se: 42.94 (43.37)

Chiral HPLC (FIG. 2) showed a single peak at RT ~10 mts (Chiral HPLC conditions-Column Nucleosil Chiral-1, 250× 4.6 mm, Flow rate at 1 ml/minute, $\lambda_{max}$ 235 nm, mobile phase was copper sulfate pentahydrate (100 mg) in 1L of water), RT for L-Se-Methylselenocysteine ~10 mts, RT for D-Se-Methylselenocysteine ~15 mts.

EXAMPLE 2

L-Se-Methyl Selenocysteine from L-Chloroalanine methyl ester hydrochloride: Dimethyldiselenide (56 g) in DMF (25 ml ) was taken to get a clear solution. NaOH solution (34 g in 150 ml water) was added under stirring. The mass was cooled to 5–10° C. and to this was added, portionwise, solid sodium borohydride (7 g) at <10 ° C. over a period of 1 hr. The reaction mixture was warmed to 40–45 ° C. and maintained for 2 hrs to get a clear colorless solution.

The reaction mixture was cooled to S C and L-chloroalanine methyl ester (25 g in 100 ml water) was added over a period of 30 mts. The solution was maintained at 5° C. for 2 hrs and at room temperature for 4 hrs. After checking the TLC for the completion of the reaction, It was acidified with 6N HCl and concentrated. Then 6N HCl was added again and concentrated. The solid was extracted with methanol. Methanol extract was neutralized with triethylamine precipitating L-Se-methylselenocysteine. This material was further purified by crystallization from waterethanol. Yield: 15 g.

EXAMPLE 3

L-Se-methylselenocysteine from L-chloroalanine hydrochloride (using hypophosphorous acid to reduce dimethyldiselenide to methane selenol): In a reaction flask equipped with a stirrer and condenser dimethylformamide (25 ml) and dimethyldiselenide (55 g) were taken under an atmosphere of nitrogen. To this solution was added slowly hypophosphorous acid (32% solution, 73 g) over a period of 30 mts. The reaction mixture was slowly heated to 70° C. and maintained for 2 hrs. The reaction mixture was cooled to 10° C. and sodium hydroxide solution (20 g in 100 ml water) was added slowly. The mixture was stirred for another 30 mts at that temperature and L-chloroalanine hydrochloride (25 g in 100 ml water) was added over a period of 1 hr. The reaction mixture was stirred for another 1 hr RT and 1 hr at 40° C. After TLC indicated completion of the reaction, the reaction mixture was worked up as in Example 4. Yield: 10 g.

EXAMPLE 4

DL-Se-Methyl Selenocysteine

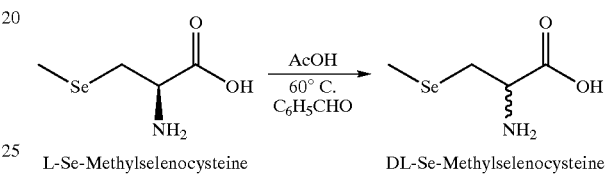

L-Se-Methylselenocysteine      DL-Se-Methylselenocysteine

A single-necked RB flask equipped with a magnetic stirring bar was charged with L-Methyl selenocysteine (0.5 g), benzaldehyde(25 mg) and acetic acid (6 ml). The resulting suspension was heated to 60° C.; After 15 minutes the reaction mixture became a clear solution. In another 20 minutes precipitation started. The mixture was stirred at this temperature for 2 hrs, then cooled to room temperature and filtered. The solid material was washed with ethanol thoroughly and dried in vacuo to afford 460 mg of white crystalline solid, DL-Se-Methylselenocysteine Yield: 460 mg, 92%; MP: 189–190° C. The chiral HPLC of this material (FIG. 1) indicated only two peaks of equal areas attesting to its racemic nature; No other peaks were detected; the peak with lower RT corresponded to L-Methyl selenocysteine.

What is claimed is:

1. A process for manufacturing L-Se-methylselenocysteine by reaction of chloroalanine methyl ester hydrochloride or chloroalanine hydrochloride or chloroalanine with methylselenol or its salts in a solvent, acidifying the reaction mixture after completion of reaction, isolating methyselenocysteine hydrochloride as a methanol solution, neutralizing the methanol solution with triethyl amine to precipitate L-Se-methylselenocysteine.

2. A process as claimed in claim 1 wherein the reaction is conducted under an inert atmosphere of nitrogen or argon.

3. A process as claimed in claim 1 wherein methylselenol or its salt is produced by reduction of dimethyldiselenide with a reducing agent chosen from sodium borohydride or hypophosphorous acid.

4. A process as claimed in claim 1, wherein dimethyldiselenide is reduced at temperature range of 0° to +60° C.

5. A process as claimed in claim 1, wherein methylselenol or methylselenide salt is reacted with chloroalanine methyl ester hydrochloride or chloroalarline hydrochloride or chloroalanine at the temperature range of 0° to +50° C.

6. A process as claimed in claim 1, wherein the solvent employed is a mixture of dimethylformamide and water.

7. A process as claimed in claim 1, wherein the solvent employed is a mixture of acetonitrile and water.

8. A process for manufacturing DL-Se-methylselenocysteine which consists of treating and solubilizing L-Se-methylselenocysteine or D-Se-methylselenocysteine in acetic acid in the presence of small quantities of benzaldehyde in the temperature range 20–100° C., cooling the reaction mixture and filtering the precipitated product namely, DL-Se-Methylselenocysteine.

* * * * *